us007550138B1

(12) United States Patent
Waters et al.

(10) Patent No.: US 7,550,138 B1
(45) Date of Patent: Jun. 23, 2009

(54) PLASMODIUM MUTANT AND VACCINES INCLUDING THE MUTANT

(75) Inventors: Andrew Paul Waters, Leiden (NL); Christofel Jan Janse, Leiden (NL); Melissa Ruth van Dijk, Leiden (NL); Robert W. Sauerwein, Nijmegen (NL)

(73) Assignees: Leiden University Medical Center, Leiden (NL); Stichting Katholieke Universiteit Nijmegen, Nijmegen (NL)

( * ) Notice: Subject to any disclaimer, the term of this patent is extended or adjusted under 35 U.S.C. 154(b) by 0 days.

(21) Appl. No.: 11/838,343

(22) Filed: Aug. 14, 2007

Related U.S. Application Data (60) Provisional application No. 60/822,297, filed on Aug. 14, 2006.

(51) Int. Cl.
*A01N 63/00* (2006.01)
*A01N 65/00* (2006.01)

(52) U.S. Cl. .................. 424/93.1; 424/93.2; 424/93.21; 424/93.7

(58) Field of Classification Search ........................ None
See application file for complete search history.

(56) References Cited

OTHER PUBLICATIONS

Xiao et al (Perlman P, Troye-Blomberg M(eds): Malaria Immunology, Chem Immunol. Basel, Karger, 2002, vol. 80, pp. 343-365).*
Frevert et al. N Engl J Med 353: (15) 1600-1602.*
Waters et al, Cell 124:689-693, Feb. 24, 2006.*
van Dijk et al. PNAS 102:12194-12199 Aug. 23, 2005.*
Clyde et al. . The American Journal of the Medical Sciences vol. 266:398-403, 1973.*
http://www.cdc.gov/malaria/pdf/clinicalguidance.pdf, Mar. 2007, pp. 1-10.*
Blaho, "Virus Infection and Apoptosis (Issue I): An Introduction," *Int. Rev. Immunol.*, 22:321-326 (2003).
Braks et al., "Development and application of a positive-negative selectable marker system for use in reverse genetics in Plasmodium," *Nucl. Acids Res.*, 34(5):e39, 12 pages (2006).
Bruña-Romero et al., "Detection of malaria liver-stages in mice-infected through the bite of a single *Anopheles* mosquito using a highly sensitive real-time PCR," *Int. J. Parasitol.*, 31:1499-1502 (2001).
Carrolo et al., "Hepatocyte growth factor and its receptor are required for malaria infection," *Nat. Med.*, 9(11):1363-1369 (2003).
Chatterjee et al. "Rodent malaria in the natural host . . . ," *Afr. J. Med. Med. Sci.*, 30:25-33 (2001).
de Koning-Ward et al., "Analysis of stage specificity of promoters in *Plasmodium berghei* using luceferase as a reporter," *Mol. Biochem. Parasitol.*, 100:141-146 (1999).
de Koning-Ward et al., "The selectable marker human dihydrofolate reductase enables sequential genetic manipulation of the *Plasmodium berghei* genome," *Mol. Biochem. Parasitol.*, 106:199-212 (2000).

Doolan and Hoffman, "IL-12 and NK Cells Are Required for Antigen-Specific Adaptive Immunity Against Malaria Initiated by CD8+ T Cells in the *Plasmodium yoelii* Model," *J. Immunol.*, 163:884-892 (1999).
Duraisingh et al., "Negative selection of *Plasmodium falciparum* reveals targeted gene deletion by double crossover recombination," *Int. J. Parasitol.*, 32:81-89 (2002).
Fidock and Wellems, "Transformation with human dihydrofolate reductase renders malaria parasites insensitive to WR99210 . . . ," *Proc. Natl. Acad. Sci. USA*, 94:10931-10936 (1997).
Franke-Fayard et al., "A *Plasmodium berghei* reference line that constitutively expresses GFP at a high level throughout the complete life cycle," *Mol. Biochem. Parasitol.*, 137:23-33 (2004).
Frevert, "Sneaking in through the back entrance: . . . ," *Trends Parasitol.*, 20(9):417-424 (2004).
Ishino et al., "Cell-Passage Activity Is Required for the Malarial Parasite to Cross the Liver Sinusoidal Cell Layer," *PLoS Biol.*, 2:77-84 (2004).
Janse and Waters, "*Plasmodium berghei*: The Application of Cultivation and Purification Techniques to Molecular Studies of Malaria Parasites," *Parasitol. Today*, 11:138-143 (1997).
Kappe et al. "Exploring the transcriptome of the malaria sporozoite stage," *Proc. Natl. Acad. Sci.USA*, 98(17):9895-9900 (2001).
Kappe et al., "*Plasmodium* Sporozoite Molecular Cell Biology," *Annu. Rev. Cell Dev. Biol.*, 20:29-59 (2004).
Khater et al., "A malaria membrane skeletal protein is essential for normal morphogenesis, motility, and infectivity of sporozoites," *J. Cell Biol.*, 167(3):425-432 (2004).
Lambros and Vanderberg, "Synchronization of *Plasmodium falciparum* Erythrocytic Stages in Culture," *J. Parasitol.*, 65:418-420 (1979).
Leirão et al, "HGF/MET signaling protects *Plasmodium*-Infected host cells from apoptosis," *Cell Microbiol.*, 7:603-609 (2005).
Leiriao et al., "Apoptic *Plasmodium*-Infected hepatocytes Provide Antigens to Liver Dendritic Cells," *J. Infect. Dis.*, 191:1576-1581 (2005).
Leitner et al., "Apoptosis is essential for the increased efficacy of alphaviral replicase-based DNA vacations," *Vaccine*, 22(11-12):1537-1544 (2004).
Le Roch et al., "Discovery of Gene Function by Expression Profiling of the Malaria Parasite Life Cycle," *Science*, 301:1503-1508 (2003).
Levine, "Eating Oneself and Uninvited Guests: Autophagy-Related Pathways in a Cellular Defense," *Cell*, 120:159-162 (2005).
Luder et al., "Intracellular protozoan parasites and apoptosis: diverse strategies to modulate parasite-host interactions," *Trends Parasitol.*, 17(10):480-486 (2001).
Luke and Hoffman, "Rationale and plans for developing a non-replicating, metabolically active, radiation-attenuated *Plasmodium falciparum* sporozoite vaccine," *J. Exp. Biol.*, 206:3803-3808 (2003).
Matuschewski et al., "*Plasmodium* sporozoite invasion into insect and mammalian cells is directed by the same dual binding system," *EMBO J.*, 21(7):1597-1606 (2002).

(Continued)

*Primary Examiner*—Robert B Mondesi
*Assistant Examiner*—Oluwatosin Ogunbiyi
(74) *Attorney, Agent, or Firm*—Banner & Witcoff, Ltd.

(57) ABSTRACT

The invention relates to the production of new *Plasmodium* mutants which are defective in the expression of the protein P36p. These mutants are unable to cause malaria, yet they can be used as vaccine, giving long lasting protection against infections with wild-type *Plasmodium*.

8 Claims, 4 Drawing Sheets

OTHER PUBLICATIONS

Menard and Janse, "Gene Targeting in Malaria Parasites," *Methods*, 13:148-157 (1997).

Menard, "Gliding motility and cell invasions by Apicomplexa: insights from the *Plasmodium* sporozoite," *Cell Microbiol.*, 3:63-73 (2001).

Morrot and Zavala, "Effector and memory CD8+ T cells as seen in immunity to malaria," *Immunol. Rev.*, 201:291-303 (2004).

Mota et al., "Migration of *Plasmodium* Sporozoites Through Cells Before Infection," *Science*, 291:141-144 (2001).

Mota et al., "Migration through host cells activates *Plasmodium* sporozoites for infection," *Nat'l. Medicine*, 8(11):1318-1322 (2002).

Mueller et al., "*Plasmodium* liver stage developmental arrest by depletion of a protein at the parasite-host interface," *Proc. Natl. Acad. Sci. USA*, 102:3022-3027 (2005).

Mueller et al., "Genetically modified *Plasmodium* parasites as a protective experimental malaria vaccine," *Nature*, 433:164-167 (2005).

Orjih et al., "Comparative studies on the immunogenicity of infective attenuated sporozoites of *Plasmodium berghei*," *Trans. R. Soc. Trop. Med. Hyg.*, 76(1):57-61 (1982).

Ozaki et al., "Simple Centrifugation Method for Rapid Separation of Sporozoites from Mosquitoes," *J. Parasitol.*, 70(5):831-833 (1984).

Restifo, "Building better vaccines: how apoptotic cell death can induce inflammation and activate innate and adaptive immunity," *Curr. Opin. Immunol.*, 12(5):597-603 (2000).

Scheller and Azad, "Maintenance of protective immunity against malaria by persistent hepatic parasites derived from irradiated sporozoites," *Proc. Natl. Acad. Sci. USA*, 92:4066-4068 (1995).

Silvie et al., "Hepatocyte CD81 is required for *Plasmodium falciparum* and *Plasmodium yoelii* sporozoite infectivity," *Nat'l Medicine*, 9(1):93-96 (2003).

Sinden, "Infection of mosquitoes with rodent malaria," *Molecular Biology of Insect Diseases Vectors: A Methods Manual*, eds. Crampton, Beard & Louis, C (Chapman and Hall, London), pp. 67-91 (1997).

Stewart and Vanderberg, "Malaria Sporozoites Leave Behind Trails of Circumsporozoite Protein During Gliding Motility," *J. Protozool.*, 35:389-393 (1988).

Stowers and Carter, "Current developments in malaria transmission-blocking vaccines," *Exp. Opin. Biol. Ther.*, 1:619-628 (2001).

Suhrbier et al., The complete development in vitro of the vertebrate phase of the mammalian malarial parasite *Plasmodium berghei*, *Trans. R. Soc. Trop. Med. Hyg.*,81:907-909 (1987).

Sultan et al., "TRAP Is Necessary for Gliding Motility and Infectivity of *Plasmodium* Sporozoites," *Cell*, 90:511-522 (1997).

Thompson et al., "Comparative genomics in *Plasmodium*: a tool for the identification of genes and functional analysis," *Mol. Biochem. Parasitol.*, 118:147-154 (2001).

Trager and Jensen, "Human Malaria Parasites in Continuous Culture," *Science*, 193:673-675 (1976).

Tsuji and Zavala, "T cells as mediators of protective immunity agains liver stages of *Plasmodium*," *Trends Parasitol.*, 19:88-93 (2003).

Tsuji et al., "Progress toward a Malaria Vaccine: . . . ," *Biol. Chem.*, 382:553-570 (2001).

van Dijk et al., "A Central Role for P48/45 in Malaria Parasite Male Gamete Fertility," *Cell*, 104:153-164 (2001).

van Spaendonk et al., "Functional Equivalence of Structurally Distinct Ribosomes in the Malaria Parasite, *Plasmodium berghei*," *J. Biol. Chem.*, 276:22638-22647 (2001).

Yuda and Ishino, "Liver invasion by malarial parasites—how do malarial parasites break through the host barrier?", *Cell Microbiol.*, 6:1119-1125 (2004).

* cited by examiner

Parasite rRNA copies in livers of BALBc mice
mean and sd

| Exp. | Irrad (n=4) | P36p⁻ (n=4) | WT (n=4) | Non-inf |
|---|---|---|---|---|
| 1 | 43.5 (57.1) | 13.8 (6.9) | $2.6 \times 10^6$ ($6.9 \times 10^5$) | |
| 2 | 34.8 (63.0) | 9.5 (8.9) | $8.9 \times 10^5$ ($7.5 \times 10^5$) | 9.3 |
| 3 | 1.5 (2.2) | 3.4 (4.8) | $1.0 \times 10^6$ ($9.2 \times 10^5$) | 275 |

SEQUENCE LISTING

```
<160> NUMBER OF SEQ ID NOS: 23

<210> SEQ ID NO 1
<211> LENGTH: 34
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 1
cgatcgatga ataatagtaa atgatgaaac gtcg                                  34

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 2
cccaagctta attacgtccc ctggatatgc                                       30

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 3
ggatatctag tgatgaggat gaatcg                                           26

<210> SEQ ID NO 4
<211> LENGTH: 28
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 4
cgcggatcca atgcttgaat acatgtgg                                         28

<210> SEQ ID NO 5
<211> LENGTH: 44
<212> TYPE: DNA
<213> ORGANISM: Artificial Sequence
<220> FEATURE:
<223> OTHER INFORMATION: Oligonucleotide primer for creating Vector

<400> SEQUENCE: 5
```

-continued

```
gtaccctcga ggctagcgat atctgatcac ccggggcggc cgcg                          44
```

<210> SEQ ID NO 6
<211> LENGTH: 44
<212> TYPE: DNA
<213> ORGANISM: Artificial Sequence
<220> FEATURE:
<223> OTHER INFORMATION: Oligonucleotide primer for creating vector

<400> SEQUENCE: 6

```
aattcgcggc cgccccgggt gatcagatat cgctagcctc gagg                          44
```

<210> SEQ ID NO 7
<211> LENGTH: 34
<212> TYPE: DNA
<213> ORGANISM: Artificial Sequence
<220> FEATURE:
<223> OTHER INFORMATION: Oligonucleotide primer with homology to hdhfr
      gene

<400> SEQUENCE: 7

```
ggaagatcta tggttggttc gctaaactgc atcg                                     34
```

<210> SEQ ID NO 8
<211> LENGTH: 33
<212> TYPE: DNA
<213> ORGANISM: Artificial Sequence
<220> FEATURE:
<223> OTHER INFORMATION: Oligonucleotide primer with homology to hdhfr
      gene

<400> SEQUENCE: 8

```
ggaagatctt taatcattct tctcatatac ttc                                      33
```

<210> SEQ ID NO 9
<211> LENGTH: 35
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 9

```
ccgctcgagc tactcataat aagaagaaga ggtac                                    35
```

<210> SEQ ID NO 10
<211> LENGTH: 35
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 10

```
ccgctcgagc tactcataat aagaagaaga ggtac                                    35
```

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 11

```
attttgcaac aattttattc ttgg                                                24
```

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer with homology to P. berghei

<400> SEQUENCE: 12
acgcattata tgagttcatt ttac                                              24

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide primer with homology to P. berghei

<400> SEQUENCE: 13
gtgtagtaac atcagttatt gtgtg                                             25

<210> SEQ ID NO 14
<211> LENGTH: 28
<212> TYPE: DNA
<213> ORGANISM: Artificial Sequence
<220> FEATURE:
<223> OTHER INFORMATION: Oligonucleotide primer with homology to P. berghei

<400> SEQUENCE: 14
cttagtgttt tgtattaatg acgatttg                                          28

<210> SEQ ID NO 15
<211> LENGTH: 19
<212> TYPE: DNA
<213> ORGANISM: Artificial Sequence
<220> FEATURE:
<223> OTHER INFORMATION: Oligonucleotide primer with homology to P. berghei

<400> SEQUENCE: 15
tttcccagtc acgacgttg                                                    19

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide primer with homology to P. berghei

<400> SEQUENCE: 16
gaaatgaata tgtcggtact atg                                               23

<210> SEQ ID NO 17
<211> LENGTH: 35
<212> TYPE: DNA
<213> ORGANISM: Artificial Sequence
<220> FEATURE:
<223> OTHER INFORMATION: Oligonucleotide primer with homology to P. berghei

<400> SEQUENCE: 17
ccgctcgagc tactcataat aagaagaaga ggtac                                  35

```
<210> SEQ ID NO 18
<211> LENGTH: 22
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 18
agtcaacaga ttattgccga tg                                            22

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide primer with homology to P.
      berghei

<400> SEQUENCE: 19
tacaaatcct aatgaattgc ttac                                          24

<210> SEQ ID NO 20
<211> LENGTH: 27
<212> TYPE: DNA
<213> ORGANISM: Artificial Sequence
<220> FEATURE:
<223> OTHER INFORMATION: Oligonucleotide with homology to P. falciparum

<400> SEQUENCE: 20
ggaccccgcg gatgtatgta ttggtgc                                       27

<210> SEQ ID NO 21
<211> LENGTH: 26
<212> TYPE: DNA
<213> ORGANISM: Artificial Sequence
<220> FEATURE:
<223> OTHER INFORMATION: Oligonucleotide with homology to P. falciparum

<400> SEQUENCE: 21
ggaccgttaa caccaaatca caaccc                                        26

<210> SEQ ID NO 22
<211> LENGTH: 30
<212> TYPE: DNA
<213> ORGANISM: Artificial Sequence
<220> FEATURE:
<223> OTHER INFORMATION: Oligonucleotide with homology to P. falciparum

<400> SEQUENCE: 22
ggaccaccgg tcctgaccct tcatcagatg                                    30

<210> SEQ ID NO 23
<211> LENGTH: 35
<212> TYPE: DNA
<213> ORGANISM: Artificial Sequence
<220> FEATURE:
<223> OTHER INFORMATION: Oligonucleotide with homology to P. falciparum

<400> SEQUENCE: 23
ggaccgggcg cccggggcca gaatgttctt gttcg                              35
```

PLASMODIUM MUTANT AND VACCINES INCLUDING THE MUTANT

RELATED APPLICATION

This application claims priority from U.S. provisional patent application No. 60/822,297, filed Aug. 14, 2006, which is hereby incorporated herein by reference in its entirety for all purposes.

REFERENCE TO A SEQUENCE LISTING

Incorporated herein by reference in its entirety is a Sequence Listing submitted as a computer readable text file of 34 kilobytes, created on [date] and identified document "05032-00138_SeqList_ST25.txt".

FIELD OF THE INVENTION

The invention relates to the field of immunology, especially to the field of the use of vaccines against infectious diseases, more in particular malaria.

BACKGROUND OF THE INVENTION

Malaria is the scourge of many developing countries, particularly those in sub-Saharan Africa, claiming several million lives each year. Malaria is caused by mosquito-borne hematoprotozoan parasites belonging to the genus *Plasmodium*. Four species of *Plasmodium* protozoa (*P. falciparum, P. vivax, P. ovale* and *P. malariae*) are responsible for the disease in humans; many others cause disease in animals, such as *P. yoelii* and *P. berghei*. *P. falciparum* accounts for the majority of lethal infections in humans. Researchers have struggled for decades to make a successful subunit or attenuated whole-organism vaccine but with limited success. Factors that have hampered the development of a subunit vaccine include the complexity of the malaria life cycle, the wide variety of immune response induced by the malaria parasite, and an incomplete knowledge of protective immunity. In contrast, attenuated whole-organism vaccines are better understood and in principle should provide full protective immunity.

Upon introduction into the bloodstream by the female Anopheline mosquito during blood feeding, the infectious sporozoite of *Plasmodium* invades and multiplies within the hepatocyte. Recognition and invasion of a hepatocyte is a complex process involving traversal through macrophage-like Kupffer cells (1) and several hepatocytes (2) before forming a parasitophorous vacuole (PV) in the final hepatocyte. Currently, only a few proteins of sporozoites have been described that play an essential role in establishing infection of the liver but are thought to be conserved in all species of *Plasmodium*. These include circumsporozoite protein (CS), thrombospondin-related anonymous protein (TRAP), microneme proteins essential for cell traversal (SPECT1, SPECT2 or PPLP1, and CelTOS) and PbIMC1a, which variously are involved in motility of sporozoites, recognition of surface receptors on host cells, and traversal and invasion of host cells (3-10). Within the PV, the sporozoite transforms and grows (trophozoite stage) and multiplies (schizont stage) for a period of a few days, resulting in the generation and release of thousands of merozoites that invade red blood cells.

The current rationale for the characterization of *Plasmodium* molecules involved in liver infection lies in the development of a (subunit) vaccine that protects against liver and subsequent blood stage infection (11). Immunization studies using complete radiation-attenuated sporozoites (RAS) showed full protection against subsequent challenge with infectious sporozoites in both animal models of malaria and in human volunteers (12). The protective immunity that is observed after immunization with RAS requires that the sporozoites infect hepatocytes and transform into the trophozoite stage (13). Such immunity is mediated by complex mechanisms involving antibody responses that inhibit sporozoite motility and host cell invasion and T cell responses directed against intrahepatocytic stages. CD4[+] T helper cells and cytotoxic CD8[+] T lymphocytes recognizing MHC presented parasite-derived peptides, as well as cytokines (IL-2, IFN-γ, and IL-12; TNF-α, IL-1, and IL-6) and nitric oxide, have been shown to be critical effectors in protection against preerythrocytic malaria (13-15).

However, vaccination studies with subunit vaccines that contain only (parts of) single proteins of sporozoites have failed so far to provide any significant, long-lasting protective immunity (11, 12). The lack of significant progress with subunit vaccines stimulated recent attempts to produce a vaccine based on the nonreplicating, metabolically active RAS (12). However, such vaccines suffer from significant drawbacks, not least the question of safety and reproducibility because the amount of radiation that generates the attenuated state is strictly defined. Parasites that are underirradiated remain infectious, and those that are overirradiated do not induce protective immunity. Recently, it has been shown that genetically attenuated sporozoites (GAS) that lack sporozoite-specific conserved genes (uis3 and uis4) that are apparently important for sporozoite development in the hepatocyte can induce significant or complete protective immunity in the *P. berghei* rodent model of malaria when different immunization protocols are used (16, 17). The use of GAS for vaccination might remove the uncertainty associated with RAS once a more thorough understanding of the mechanisms of immunity invoked by GAS and their developmental defect(s) are available.

Although the currently developed uis3[−] and uis4[−] *Plasmodium* mutants show promising results, there is always need for better and/or alternative genetically attenuated mutants that give a protective response in malaria.

SUMMARY OF THE INVENTION

It has now been surprisingly found that *Plasmodium* mutants which are defective in producing the P36p protein are excellent candidates for a vaccine against malaria. Therefore, the present invention comprises a mutant of *Plasmodium* wherein expression of the protein P36p has been disrupted, preferably wherein said disruption has been achieved by complete or partial deletion of the gene coding for said protein P36p.

In another embodiment of the invention in such a mutant further the expression of the protein P36, the protein Uis3 and/or the protein Uis4 has been disrupted, preferably by complete or partial deletion one or more of the genes coding for proteins P36, Uis3 and Uis4.

The *Plasmodium* mutant of the invention is preferably a mutant of and species of *Plasmodium* that might serve as a vaccine in humans or act as a model system for the grater elucidation of the interface between the parasite and the host immune system. Examples of the immediately desired species in which the mutant might be generated and their different applications are: *Plasmodium falciparum* (human vaccination) *Plasmodium berghei* or *Plasmodium yoelii* model); *Plasmodium knowlesi* (human vaccination/model).

In another embodiment the invention comprises an immunological composition comprising the mutant of the invention.

Yet another embodiment of the invention is a vaccine for prevention or treatment of malaria comprising the mutant of the invention and a pharmaceutically acceptable carrier and optionally an adjuvant.

Also part of the invention is a method for preventing or treating malaria wherein the immunological composition of the invention or the vaccine of the invention is administered to a subject, which subject is preferably human.

Further part of the invention is the use of the mutant of the invention as a delivery system for heterologous vaccination against other diseases and other stages of the malaria parasite.

LEGENDS TO THE FIGURES

FIG. 1. Generation of the p36p⁻ parasite lines. (A) Schematic representation of the p36p⁻ locus on chromosome 10 (containing p36 and the paralogue p36p) (20) and the replacement vector MI4. Correct integration of the construct results in the disrupted p36p gene as shown. Open box, untranslated regions; black box, pb36p and pb36 coding regions; gray box, tgdhfr/ts SC. (B) Disruption of p36p was shown by PCR (Right) and by Southern analysis of separated chromosomes (Left). PCR on DNA of WT and p36p⁻ clones (KO1 and KO2) results in the amplification of a 1.2-kb WT fragment and a 1.0-kb disrupted fragment. Chromosomes hybridized to a $P.$ $berghei$ (pb) dhfr/ts 3' UTR region (DT-3') specific probe detect the endogenous dhfr/ts copy on chromosome 7 and the integrated construct on chromosome 10. (C) The absence of p36p transcripts in p36p⁻ parasites as shown by RT-PCR on RNA from WT and p36p⁻ sporozoites with (+) or without (−) reverse transcriptase. (D) Schematic representation of the gfp insertion construct pl0019 and the cssu of the rRNA gene unit on chromosome 5 that serves as target locus for integration of the gfp vector by a single crossover. Black box, cssu; gray box, hdhfr SC; open box, gfp expression cassette. (E) Correct integration of the gfp construct in the genome of p36p⁻ parasites (KO1) shown by PCR (Right) and by Southern analysis of separated chromosomes (Left). PCR on DNA of WT and p36p⁻ gfp parasites (KOGFP) results in the amplification of a 3-kb WT fragment, a 3-kb fragment of the disrupted cssu, and a 1-kb fragment of the disrupted p36p locus. Separated chromosomes were hybridized to the DT-3'-probe, detecting pbdhfr/ts on chromosome 7, the gfp construct on chromosome 5, and the MI4 construct on chromosome 10. (f) GFP-fluorescent oocysts and sporozoites (Left) and blood stages (Right) of the p36p⁻gfp parasites.

DETAILED DESCRIPTION OF THE INVENTION

P36p is a sporozoite-specific protein (18 and 19), which is a member of a small family of 10 $Plasmodium$ surface proteins, the P48/45 family, that include other promising vaccine candidate antigens, such as P48/45 and P230, that are expressed on the surface of gametes (20-22). P36p has no function in sporozoite motility and invasion of both salivary glands and hepatocytes, and instead plays an essential role during development of the liver trophozoite. Thus, it is one of many essential genes of $Plasmodium$.

Although genetically attenuated strains of $Plasmodium$, which induce a protective immune response are known, these mutants of the prior art are defective in genes, which appear to be "upregulated in infective sporozoites", hence the names UIS3 and UIS4. It was contemplated, that since these genes were upregulated in infective sporozoites, disruption of these genes would render the mutants unable to establish an infection in the host and thus useful as whole-organism vaccine.

It is however, beforehand, impossible to predict whether mutants with respect to any of the UIS genes would be useful. Many of the UIS genes will not be critical genes, which means that deletion of such a gene or its gene product does not produce an attenuated parasite. Hence, such a mutant would still be able to cause disease. Further, even if an UIS gene would appear to be critical, use of a mutant for this gene would not necessarily give a protective response.

Development of p36p⁻ parasites aborts within the hepatocyte and P36p⁻ parasites apparently fail to maintain a parasitophorous vacuole, arresting early during intrahepatocytic development. P36p-deficient parasitized cell numbers are progressively reduced after 24 h in culture and in vivo and apparently fail to prevent host cell apoptosis, consequently leading to parasite clearance. Yet, as is shown herein, immunization with p36p⁻ sporozoites induces protective immune responses against subsequent challenges with wild-type sporozoites.

Interestingly, as has been shown for RAS, only a single immunizing dose of p36p⁻ sporozoites is required to elicit a long-lasting protective immune response in BALB/c mice (40) and induces a protective immune response that is parasite stage specific (16, 17). As in the immunization studies performed with uis3⁻ and uis4⁻ GAS (16, 17) and RAS (40), three immunizing doses of p36p⁻ sporozoites are required to completely protect C57BL6 mice for minimally 1 month. Intriguingly, p36p⁻ sporozoites, like uis4⁻ GAS, albeit at a lower frequency, initiated a delayed blood stage infection in some mice, but only when p36p⁻ sporozoites are inoculated i.v.

Like GAS, RAS sporozoites invade liver cells and transform into the rounded trophozoite stage, but do not enter the process of schizogony. However, trophozoite development of RAS arrests at a later stage and produces a visible PV compared to p36p⁻ sporozoites. Moreover, RAS-infected hepatocytes persist in culture longer than their GAS-infected counterparts, which, in the case of p36p⁻ parasites, results from their failure to prevent the host cell from entering apoptosis. Although RAS populations provoke apoptosis to a greater degree than WT sporozoites, they do so to a significantly lower degree than p36p⁻ sporozoites. We also determined in vivo the persistence of RAS- and p36p⁻-infected hepatocytes in whole liver extracts of BALB/c mice by using real-time PCR for liver schizont detection (36). Our results confirm the significantly more rapid clearance of p36p⁻ parasitized hepatocytes within 6 h after infection compared to RAS-infected hepatocytes as has been observed in vitro (data not shown). However, similar low numbers of RAS- and p36p⁻-infected hepatocytes are observed 1 week after infection.

Immune responses against RAS are complex and involve both cell-mediated and humoral immunity (13-15). However, the differing biological characteristics of RAS and GAS described here suggest that the immune responses elicited by RAS and GAS could be different. For example, cell death by apoptosis was originally described to occur in the absence of inflammation. Interestingly, in the context of infection, apoptosis is being redefined based on a number of studies demonstrating that apoptotic death of host cells after pathogen infection can trigger powerful innate and adaptive immune responses. In fact, apoptosis-induced inflammation is actively being investigated as a way of enhancing vaccine function improving accessibility of the effector cells of the immune system to the site of infection (41, 42). Moreover, presentation of parasite antigens in the context of host cell apoptosis has recently been shown as an alternative mechanism involved in the induction of protective immunity by RAS (43). As apoptosis of p36p⁻-infected hepatocytes was also detected in vivo, it might well be that host-cell apoptosis is associated with the ability of p36p⁻ sporozoites and other GAS to induce protective immune responses and needs further investigation.

The mechanisms and (parasite) molecules involved in preventing host cell apoptosis by intracellular parasites including apicomplexans are being investigated (44, 45). Recently, it has been shown that *Plasmodium* parasites exploit the host molecule hepatocyte growth factor (HGF), secreted exclusively by hepatocytes damaged by parasite transit (32), to activate anti-apoptotic signaling pathways in the host cell through HGF/MET signaling (34). The ability of the p36p⁻ sporozoites to invoke this pathway is currently unknown.

Furthermore, our studies show that p36p⁻ sporozoites are able to invade hepatocytes but seem to be unable to produce a mature PVM (parasitophorous vacuole membrane) which might be a critical step in the intracellular survival of the parasite. It might well be that the presence of a PVM is essential in escaping from host defense mechanisms (avoiding internal cellular surveillance by the hepatocyte). Indeed, if the parasite enters the host cell either without a PVM or with an incomplete PVM, infection may be readily detected by the host cell, and this may in turn trigger xenophagy, leading ultimately to an inflammatory apoptotic response (46). Therefore, the attenuated parasite may survive only as long as either the killing response of the host cell allows or the parasite can avoid or neutralize the host cell defense mechanisms.

P36p may be essential for intracellular survival/development through being involved in an essential preceding step affecting gene-expression through signalling; therefore, the absence of P36p results in the lack of the necessary parasite mediators that control parasite survival, formation and/or maintenance of an effective PV, and direct involvement in the regulation of the host cells apoptotic machinery. Interestingly, P36p is anticipated to be a GPI-anchored membrane protein and, therefore, may play a role in the interactions between the developing trophozoite and its host cell.

In the present invention *Plasmodium berghei* mutants have been shown to induce protective immunity in a rodent model of malaria. Since *Plasmodium berghei* and *Plasmodium falciparum*, which is the causative agent for malaria in humans, are very similar in genetic and morphologic structure, and since the infection by *P. berghei* in mice and *P. falciparum* in humans share many features and results with RAS are comparable, it is postulated that p36p⁻ mutants of *P. falciparum* are equally able to provide long-lasting protective immune responses in humans.

Next to the p36p gene, *Plasmodium* also contains a close paralogue gene p36. This gene is located directly adjacent to p36p in the parasite genome, and it appears that it is also expressed in sporozoites. However, apparently in our experiments, the P36 protein is not able to replace the full function of the P36p protein, since otherwise normal infection by the p36p⁻ mutant would take place. The presence of P36 might explain the difference in host immune response to P36p⁻ GAS. Furthermore, it is imaginable that a spontaneous mutation would occur in the p36p– mutants, which would cause full complementation by the P36 protein (or the expression of a functional P36p protein), as a result of which the mutant would again be able to cause malaria. To circumvent these options, the mutant of the invention preferably comprises one or more further mutations in the genome. Such a mutation could be the knock-out of the p36 gene-expression, or the knock-out of expression of any of the "upregulated in infective sporozoites" (UIS) genes, preferably UIS3 or UIS4. Said knock-outs may be produced in an analogous manner to the p36p– mutant, i.e. by deleting or replacing (part of) the gene. Of course, the person skilled in the art may know other ways of inhibiting expression of the p36p, p36, UIS3 and UIS4 genes, although the application in *Plasmodium* of commonly practiced alternatives such as anti-sense expression or RNAi remains controversial. The most reliable manner to achieve multiple sequential deletions of genes in *Plasmodium* utilises methodologies developed recently and will leave no foreign DNA in the resulting mutant parasite. The technologies were developed by the proposing laboratory and are unique to this laboratory [Braks, J. A. M., Franke-Fayard, B., Kroeze, J., Janse, C. J. & Waters, A. P. (2006) Nucl. Acids Res. 34 e39. Development and application of a positive-negative selectable marker system for use in reverse genetics in *Plasmodium*.] It is contemplated that any mutant which lacks expression of the genes discussed above, irrespective of the way such lack of expression is engineered, would be useful in the present invention.

Next to the use of the mutants as such for combating or preventing disease-producing effects of the wild-type parasites, the mutants may also be used as a carrier (vector) for heterologous antigens. The genetic information coding for one or more heterologous antigens may be inserted in the mutant parasites of the invention by conventional genetic engineering techniques. It is, for example, possible to insert a gene coding for an antigen in the place of the p36p gene, or, alternatively, the gene coding for the antigen may be inserted at any other place in the *Plasmodium* genome. Preferably, the gene encoding a heterologous antigen is placed after a promoter which ensures expression during the sporozoite phase.

In the same sense, the mutants of the invention can also be used as carriers for antigens of *Plasmodium*, which normally would only be exposed during the later life cycle of the parasite, e.g. that are specific for the trophozoite stage.

The mutants of the invention may be comprised in an immunological composition, i.e. a composition which is able to trigger the immune system of the subject to which it is administered. Preferably, such an immunological composition is a vaccine.

The invention pertains to a vaccine composition comprising a mutant according to the invention. This mutant is intended to be delivered as a live but attenuated organism with no adjuvant. Previous work with RAS indicates that irradiated sporozoites that receive sufficient irradiation to kill not disable the infectivity of the parasite no longer induce protective immune responses.

In order to ensure optimum performance of such a vaccine composition it is preferred that it comprises an immunologically and pharmaceutically acceptable carrier, vehicle and/or adjuvant.

An effective vaccine, wherein a protein of the invention is recognized by the animal, will in an animal model be able to prolong survival times and/or diminish weight loss after challenge with a malarial parasite, compared to non-vaccinated animals.

The mutants of the invention as described above may be formulated together with carriers, such as, for example, liposomes, oil in water emulsions, and or metallic salts, including aluminium salts (such as aluminium hydroxide). However, care should be taken to use only those formulations, which would sustain the sporozoites, since they need to be alive for properly invoking the immune response. Vaccine preparation is generally described in New Trends and Developments in Vaccines, edited by Voller et al., University Park Press, Baltimore, Md., U.S.A. 1978.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient (mutant parasite) per vaccination with a preferred range from about $10^3$-$10^7$, but preferably $10^4$-$10^5$ sporozoites per vaccination dose, when administered intravenously(12). Suitable regimens for initial administration and booster shots are also variable but are typified by an initial administration followed by subsequent inoculations or other administrations.

In many instances, it will be necessary to have multiple administrations of the vaccine. Especially, vaccines can be administered to prevent an infection with malaria and/or to treat established malarial infection. When administered to prevent an infection, the vaccine is given prophylactically, before definitive clinical signs or symptoms of an infection are present. Protocols have been established for the administration of attenuated sporozoite vaccines (summarized in Luke and Hoffman ibid) and would serve as a preliminary platform for the further definition of the ideal dose administration, size and frequency.

The invention also pertains to a method for immunizing an animal, including a human being, against malaria caused by e.g. *P. falciparum*, comprising administering to the animal the mutant of the invention, or a vaccine composition of the invention as described above.

The invention also pertains to a method for producing an immunologic composition according to the invention, the method comprising preparing, synthesising or isolating a mutant according to the invention, and solubilizing or dispersing said mutant in a medium for a vaccine, and optionally adding other antigens and/or a carrier, vehicle and/or adjuvant substance.

EXPERIMENTAL PART

Example 1

Generation of the p36p⁻ Parasite Lines

To disrupt the p36p locus a p36p replacement vector was constructed in vector b3D.D$_T$.^H.^D$_t$, containing the pyrimethamine-resistant *Toxoplasma gondii* (tg) dhfr/ts gene. To introduce gfp into the genome of p36p⁻ parasites, a vector was constructed with the human (h) dhfr selectable marker and gfp under control of the constitutive pbef-1aa promoter (23-25) and a fragment of 2 kb of the D-type small subunit (dssu) rRNA gene of *P. berghei* (22). The linearized vector can integrate in C-type small subunit (cssu) and/or dssu. Integration into cssu does not affect the phenotype of the parasites (26).

Construction of a Replacement Vector to Disrupt the p36p Locus.

To disrupt the p36p locus, a p36p replacement vector was constructed in vector b3D.D$_T$.^H.^D$_b$, containing the pyrimethamine resistant *Toxoplasma gondii* (tg) dhfr/ts gene. P36p targeting sequences flanking the selection cassette (SC) were amplified by PCR from *Plasmodium berghei* genomic DNA by using primers L903 (5'-CGATCGATGAATAATAG-TAAATGATGAAACGTCG-3 (SEQ ID NO:1) and L904 (5'-CCCAAGCTTAATTACGTCCCCTGGATATGC-3 (SEQ ID NO:2), and primers L905 (5'-GGATATCTAGTGATGAG-GATGAATCG-3 (SEQ ID NO:3) and L906 (5'-CGCG-GATCCAATGCTTGAATACATGTGG-3 (SEQ ID NO:4). PCR fragments were inserted up- and downstream of the SC, resulting in MI4. The fragment used for disruption of p36p was obtained after digestion of MI4 with ClaI/BamHI.

Construction of an Insertion Vector to Introduce gfp into the Genome of p36p⁻ Parasites.

To introduce gfp into the genome of p36p⁻ parasites a vector was constructed with the human (h) dhfr selectable marker and gfp under control of the constitutive pbef-1aa promoter (23) and a fragment of 2 kb of the d-type small subunit (dssu) rRNA gene of *P. berghei* (23). The pbef-1a promoter region (pE(A)b.luc.^D) (24) was subcloned as a 0.6-kb HindIII/NdeI fragment in pBluescript II KS (HindIII/SmaI). After deletion of the EcoRI site, the promoter was cloned (HindIII/BamHI) into pD$_b$.D$_h$.^D$_b$ (25) to create pDEF. Primers L972 (5'-GTACCCTCGAGGCTAGC-GATATCTGATCACCCGGGGCGGCCGCG-3) (SEQ ID. NO:5) and L973 (5-AATTCGCGGCCGCCCCGGGTGAT-CAGATATCGCTATCGCTAGCCTCGAGG-3) (SEQ ID NO:6) were annealed and cloned in the EcoRI and Asp718 sites of pDEF to obtain pDEF-EA. The hdhfr was PCR amplified using primers L886 (5'GGAAGATCTATGGTTGGT-TCGCTAAACTGCATCG3 (SEQ ID. NO:7) and L887 (5'GGAAGATCTTTAATCATTCTTCTCATATACTTC3') (SEQ ID. NO:8) and cloned in pDEF-EA (BamHI). Finally, the tgdhfr/ts SC of PbGFPcon (23) was replaced by the hdhfr SC of pDEFhD-EA to create pl0019. The linearised vector can integrate in c- and/or dssu.

*P. berghei* wild-type (WT) parasites (clone 15cyl; ANKA strain) were used to generate p36p⁻ parasites. Transfection, selection, and cloning of p36p⁻ parasites was performed as described (27). Two independent transfection experiments were performed, and two clones (KO1 and KO2) were selected for further analysis. p36p⁻ parasites (KO1) were transfected with the gfp vector to create p36p⁻ mutants expressing gfp constitutively throughout the life cycle. Selection of transformed parasites was performed by treating infected animals with WR99210 (16 mg/kg bodyweight) as has been described (25). One parasite clone (KOGFP) in which the gfp was integrated into the cssu was selected for further analysis. Correct integration of constructs into the genome of transformed parasites was analyzed by RT-PCR and Southern analysis of restricted DNA or separated chromosomes by field inversion gel electrophoresis (27). PCR on DNA of WT and p36p⁻ parasites was performed by using primers specific for the WT (L1362 5'-CCGCTCGAGACCT-TAGGACACTTTGAAATTTG-3' (SEQ ID NO:9) and L1363 5'-CCGCTCGAGCTACTCATAATAAGAAGAA-GAGGTAC-3' (SEQ ID NO:10); amplifying a fragment of 1.2 kb) and disrupted (L1389 5'-ATTTTGCAACAATTT-TATTCTTGG-3' (SEQ ID NO:11) and L313 5'-ACGCAT-TATATGAGTTCATTTTAC-3' (SEQ ID NO:12); amplifying a fragment of 1.0 kb) locus. PCR on DNA of WT and p36p⁻: gfp parasites was performed by using primers specific for WT (L270 5'-GTGTAGTAACATCAGTTATTGTGTG-3' (SEQ ID NO:13) and L271 5'-CTTAGTGTTTTGTATTAATGAC-GATTTG-3' (SEQ ID NO:14), amplifying a fragment of 3 kb) and disrupted cssu (L270 and L635 5'-TTTCCCAGTCAC-GACGTTG-3' (SEQ ID NO:15), amplifying a fragment of 3 kb). Primers 1389 and 313 amplified the expected fragment of 1.0 kb of the disrupted p36p locus in KOGFP parasites. RT-PCR was performed on RNA isolated from WT and p36p⁻ sporozoites as described by Invitrogen. To amplify cDNA derived from the p36p⁻ or circumsporozoite (CS) gene, primers L1425 (5'-GAAATGAATATGTCGGTACTATG-3') (SEQ ID NO:16) and L1363 (5'-CCGCTCGAGCTACTCAT-AATAAGAAGAAGAGGTAC-3') (SEQ ID NO:17), amplifying a fragment of 0.5 kb, and L1502 (5'-AGTCAACAGAT-TATTGCCGATG-3') (SEQ ID NO:18) and L1503 (5'-TACAAATCCTAATGAATTGCTTAC-3') (SEQ ID NO:19), amplifying a 0.8-kb fragment, were used, respectively.

Phenotype Analysis of the p36p⁻ Parasite During Blood Stage and Mosquito Stage Development.

The phenotype of blood stage development was analyzed in asynchronous infections in Swiss mice and during standardized synchronized development in vivo and in vitro as described (28). Gamete formation, fertilization and ookinete production were studied in vitro as described (20). Oocyst formation and sporozoite development were investigated by using *Anopheles stephensi* and standard methodologies (29). The number of sporozoites per salivary gland was determined by mixing the salivary glands of 10 infected mosquitoes in 300 μl of PBS and counting the numbers of sporozoites in duplicate in a cell counter.

Analysis of Characteristics of the Infectivity of p36p⁻ Sporozoites.

The capacity of p36p⁻ sporozoites to establish blood stage infections was established by infection of mice (female BALB/c and C57BL6, 15-20 g) through bites of infected mosquitoes or i.v. injection of $5\times10^4$ purified sporozoites, dissected from infected mosquito salivary glands (30), per mouse. Twenty to 40 infected mosquitoes were allowed to feed on each mouse 20 days after the infectious blood meal. Blood stage infections were monitored in Giemsa-stained bloodsmears or by FACS analysis of tail blood when p36p⁻: gfp parasites were used (23) on days 4-14 after infection. Infection with WT sporozoites results in a 1-10% parasitemia at day 4-6 after mosquito feeding and a 0.5-5% parasitemia on day 4 or 5 after i.v. injection.

Gliding motility of sporozoites was analyzed by counting the average number of circles performed by single sporozoites (31). Sporozoites ($4\times10^4$) were spun for 10 min at 1,800×g onto glass coverslips previously coated with 0.02% gelatin in water, followed by incubation for 2 h at 37° C. and staining with anti-CS 3D11 antibody (Ab) for sporozoite and trail visualization. Quantification was performed by counting the average number of circles performed by 100 sporozoites in three independent coverslips. Hepatocyte invasion and traversal were studied in vitro by adding purified sporozoites to confluent monolayers of HepG2 cells in supplemented MEM medium as described (32). Cell traversal was quantified by counting parasite-wounded hepatocytes using a cell-impermeant fluorescent tracer macromolecule, rhodamine-dextran (1 mg/ml) (2). Hepatocyte invasion was determined by counting the percentage of sporozoites inside dextran-negative cells as described (33). Sporozoite development within HepG2 cells in vitro was determined by staining cells using different Abs: anti-PbEXP-1, detecting a PVM-resident protein (V.H., unpublished results); and anti-HSP90 (V.H., unpublished results) or anti-HSP70 (2), detecting the parasite cytoplasmic heat shock protein 90 or 70, respectively. Cells were stained with DAPI to visualize the nuclei. Trophozoite development was quantified by counting the numbers of trophozoites 24 h after invasion of sporozoites in a whole coverslip.

In Vitro Analysis of Apoptosis in RAS and p36p⁻ Parasite-Invaded Hepatocytes.

Two distinct fluorescent methods for apoptosis detection were used: (i) active caspase-3 detection, and (ii) nuclear morphology by DAPI staining as described (34). A total of $3\times10^4$ sporozoites (WT, p36p⁻, or RAS; gamma source, 16 Krad, ref. 35) were added to monolayers of $2\times10^5$ HepG2 cells (DMEM/10% FCS/1% penicillin/streptomycin/1 mM glutamine) for 6 h before staining with anti-HSP70 Ab (2) for parasite detection. Apoptotic cells were visualized 6 h after infection by using an active caspase-3 detection kit (Promega) and DAPI staining. Infection and apoptosis rates were quantified by counting the number of parasite-infected cells per coverslip and apoptotic parasite-infected cells per coverslip respectively, in triplicate.

In Vivo Analysis of Apoptosis in p36p⁻ Parasite-Invaded Hepatocytes.

Two C57BL/6 mice per group were infected with $5\times10^5$ p36p⁻ or WT sporozoites by i.v. injection. Livers were removed 6 h after infection and snap-frozen, and 20 histological sections from each mouse were stained for both parasite detection (anti-HSP70; ref. 2) and nuclear morphology by DAPI staining. All sections were examined for the presence of infected cells with signs of apoptosis.

Analysis of the Immunization Potential of p36p⁻ Sporozoites.

Groups of BALB/c and C57BL6 mice were immunized by i.v. injection of p36p⁻ sporozoites or RAS (35) or PBS and monitored for blood stage parasitaemia in Giemsa-stained bloodsmears. Mice were challenged with different doses of WT sporozoites on different time points. Animals were either monitored for blood stage parasitemia in bloodsmears every other day starting from day 3 to 3 weeks after challenge or killed 40 h after challenge for liver extraction and quantification of infection by real-time PCR quantification of A-type 18S ribosomal RNA copies (36). For each set of experiments, groups of naïve mice were included to verify infectivity of the sporozoite challenge dose.

Generation and Characterization of p36p⁻ and p36p⁻:gfp *P. berghei* Parasites.

Figure 1:
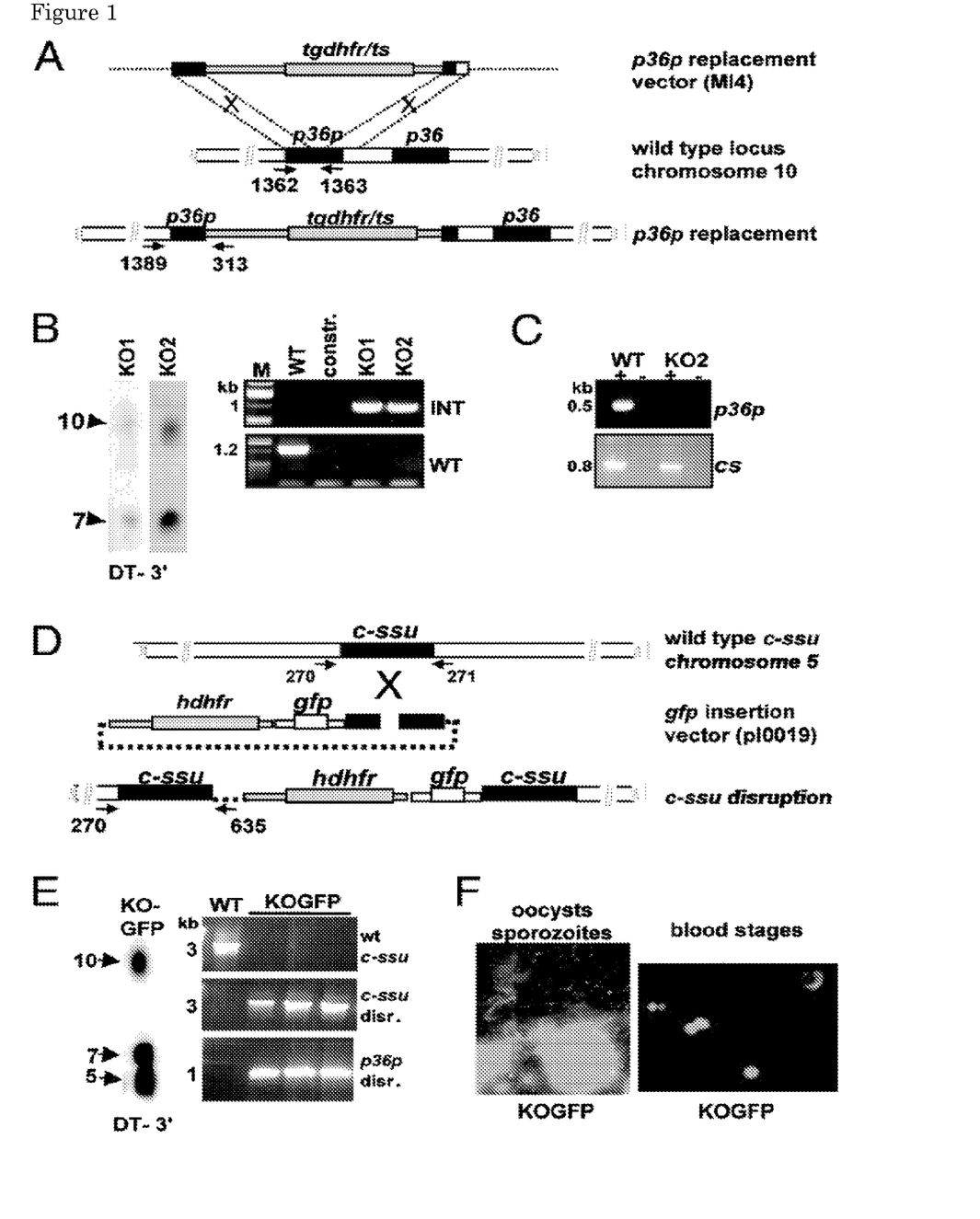

To investigate the function of P36p, we created two independent, cloned lines of *P. berghei* parasites that are deficient in P36p (p36p⁻) by using targeted disruption of the P36p gene through double crossover homologous recombination (27)

(FIG. 1). In addition, to better visualize and count the p36p⁻ parasites, we introduced gfp under control of a constitutive promoter in the genome of one of the p36p⁻ lines (p36p⁻:gfp; FIG. 1). The inability of the p36p⁻ parasites to produce transcripts of p36p and thus express P36p in sporozoites was shown by RT-PCR (FIG. 1). All three p36p⁻ lines show no phenotype that is different from WT parasites during blood stage development (results not shown) and development in the mosquito. The characteristics of fertilization and zygote development as well as oocyst and sporozoite production in the mosquito were not affected in the independent p36p⁻ lines (Table 1).

rocyte-infectious merozoites (37). p36p⁻ sporozoites were able to traverse and infect hepatocytes as well as WT sporozoites (Table 1).

Sporozoite invasion of hepatocytes requires sporozoite apical secretion, permitting the subsequent formation of a PV within which the developing parasite resides (38). Induction of apical secretion by incubation of sporozoites with HepG2 cell extracts showed that both WT and p36p⁻ sporozoites present a similar level of activation of the apical complex (data not shown). Immunofluorescent antibody test analysis revealed that WT sporozoites generate a clearly visible PV membrane (PVM) formation containing PbExp1, a PVM-

TABLE 1

Mosquito development, gliding motility, hepatocyte traversal, and invasion of p36p⁻ sporozoites

| Parasite | Ookinete production in vitro, *% | Oocyst, no. mean (range)† | Sporozoite no. per salivary gland† | Mosquito infection, no of mice infected‡ | Sporozoite injection: no of mice infected§ | Gliding motility¶ | Traversal through cells‖** | Hepatocyte invasion** | Liver trophozoites at 24 h**†† |
|---|---|---|---|---|---|---|---|---|---|
| WT | 78% (60-85) | 165 (8-200) | 114,000 | 4 (4) | 5 (5) | 4.1 ± 1.2 | 38.3 ± 7.6 | 32.4 ± 14.9 | 248 ± 8.1 |
|  |  | 174 (21-230) | 72,000 | 4 (4) | 15 (15) | 6.4 ± 2.1 | 26.2 ± 5.6 | 38.5 ± 12.9 | 330 ± 20.1 |
| KO1 | 69% (60-75) | 210 (120-350) | 128,000 | 0 (5) | 0 (3) | 4.3 ± 1.3 | 37.3 ± 15.4 | 30.1 ± 9.2 | 1.3 ± 1.5 |
|  |  | 183 (112-240) | 99,000 | 0 (3) | 0 (15) |  |  |  |  |
| KO2 | 75% (65-80) | 120 (35-160) | 108,000 | 0 (4) | 0 (3) |  |  |  |  |
| KOGFP | 66% (55-70) | 160 (20-260) | 98,000 | 0 (2) | 0 (20) | 6.1 ± 2.3 | 27.6 ± 1.2 | 39.7 ± 16.3 | 0 |

*Percentage of female gametocytes that transform into ookinetes in vitro under standard culture conditions as described (19).
†Mean number (and range) of oocysts in mosquitoes at day 10 after feeding on infected mice and mean number of sporozoites per salivary gland in glands dissected from mosquitoes at day 20 after the infectious blood meal.
‡Number of mice that became positive after feeding of 20-40 infected mosquitoes at day 20 after the infectious blood meal. The total number of mice that were exposed to mosquito infection are shown in parentheses. In experiments using WT parasites, all mice became positive with a parasitemia of 1-10% on day 4 or 5 after infection.
§Number of mice that became positive after i.v. injection of $5 \times 10^4$ sporozoites. The total number of mice that were injected with sporozoites are shown in parentheses. In experiments using WT sporozoites, all mice became positive with a parasitemia of 0.5-5% on day 4 or 5 after infection.
¶The gliding motility of sporozoites is defined as the average number of circles performed by a single sporozoite.
‖The capacity of sporozoites to traverse hepatocytes is defined as the percentage of dextran positive hepatocytes in vitro 2 h after adding sporozoites to hepatocytes.
**Hepatocyte invasion was determined by counting the number dextran-negative hepatocytes containing sporozoites, 2 h after adding sporozoites to hepatocytes in vitro.
††Parasite development in hepatocytes was determined by counting trophozoites present at 24 h after invasion of sporozoites into hepatocytes in vitro.

P36p is Essential for Sporozoite Development within the Hepatocyte.

The infectivity of p36p⁻ sporozoites to the host (BALB/c and C57BL6 mice) was strongly affected, as was shown by the complete absence of a blood stage infection after infection through the bite of mosquitoes or after i.v. inoculation of purified salivary gland sporozoites (Table 1). However, occasionally, some mice from both host strains (10% C57BL6, i.e., 5 of 48 mice; 4% BALB/c, i.e., 1 of 26 mice) did develop a 7-day delayed blood stage infection upon i.v. injection of p36p⁻ sporozoites in a parasite dose-independent fashion (data not shown). Interestingly, blood stage infections were never observed when p36p⁻ sporozoites were transmitted naturally through mosquito bites. The resulting blood stage parasites still contained the knockout genotype, as analyzed by PCR (data not shown).

Gliding motility is a feature of *Plasmodium* sporozoites and associated with invasion of both salivary glands and hepatocytes (4). p36p⁻ sporozoites are unaffected in their ability to glide (Table 1) and, therefore, the loss of infectivity of these sporozoites is not due to disrupted motility.

Figure 2:
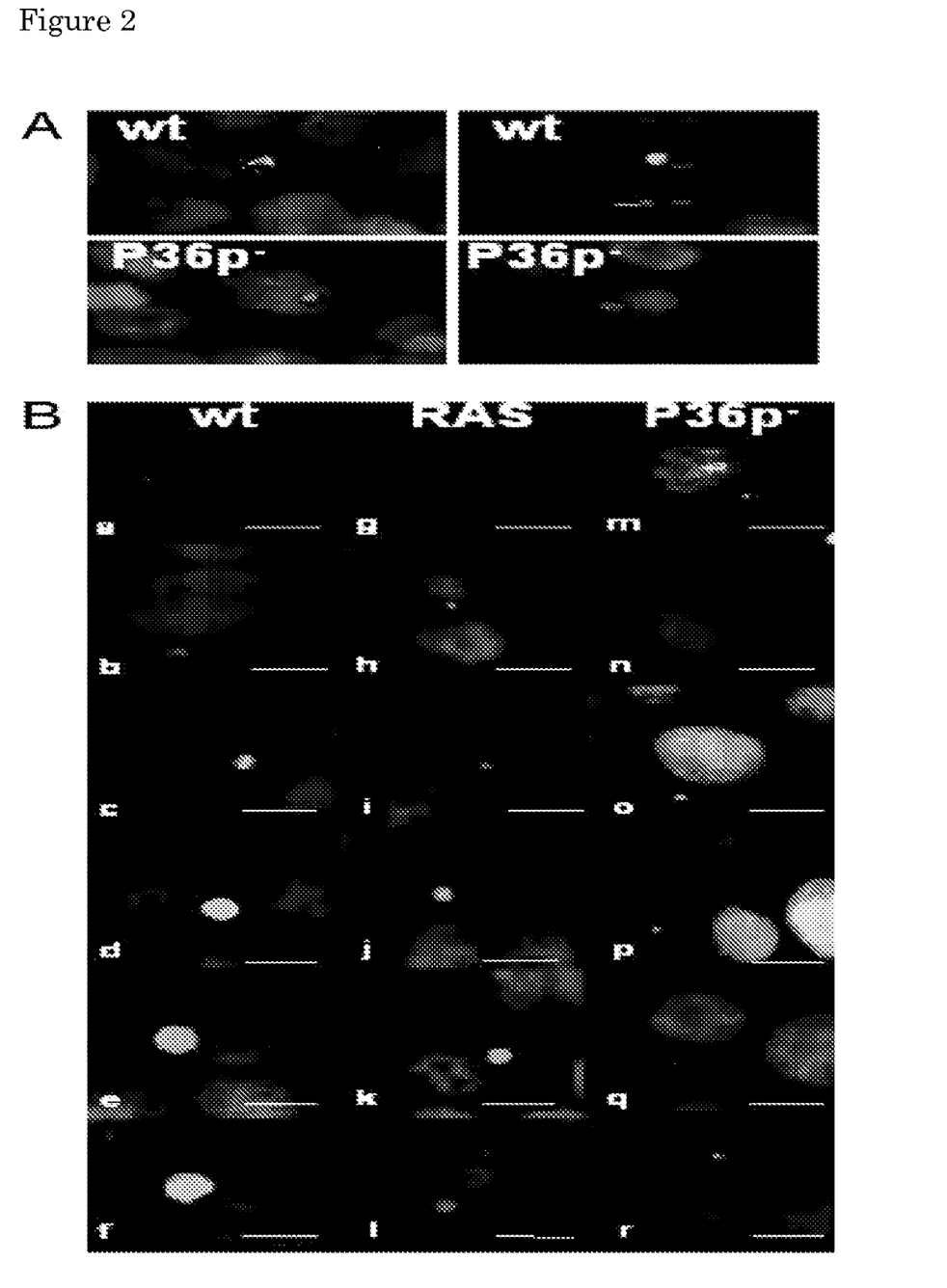
FIG. 2. Development of WT, RAS, and p36p⁻ sporozoites in hepatocytes in vitro. Cells were stained by using anti-PbEXP-1 to detect the PVM, anti-HSP90, or HSP70 to visualize the parasite cytoplasm and DAPI to stain the nuclei (blue fluorescence). (A) Visualization of the PVM (green, anti-PbEXP-1) in trophozoites of WT and p36p⁻ parasites (red, anti-HSP90) at 15 and 24 h after infection, respectively. (B) Trophozoite development of WT (a-f), RAS (g-l), and p36p⁻ (m-r) parasites at 6, 12, 15, 18, 21, and 24 h after invasion using anti-HSP70 (green; bar, 10 μm).

We analyzed the ability of p36p⁻ sporozoites to traverse and infect human hepatocyte cells (HepG2) in culture. HepG2 cells support full exoerythrocytic development of *P. berghei* sporozoites into mature schizonts containing erythrocyte-infectious merozoites (37). resident protein, in infected HepG2 cells that is completely absent in HepG2 cells at 15 and 24 h after infection by p36p⁻ sporozoites (FIG. 2). In sharp contrast to WT sporozoites, which gave rise to mature schizonts after 60-72 h of in vitro culture in HepG2 cells, p36p⁻ sporozoites develop poorly (FIG. 2), and most parasitised hepatocytes could no longer be detected after 24 h (Table 1). Equal numbers of p36p⁻, RAS, and WT sporozoites were observed in dextran-impermeant hepatocytes; therefore, p36p⁻ sporozoites might initiate but not maintain a PVM in HepG2 cells.

The aborted development of p36p⁻ sporozoites shows several similar characteristics to the aborted development of RAS, yet trophozoite development of p36p⁻ parasites is aborted at an earlier stage compared to RAS (FIG. 2).

p36p⁻ Sporozoite-Infected Hepatocytes Enter Apoptosis More Frequently than RAS or WT Parasite-Infected Hepatocytes.

Figure 3:
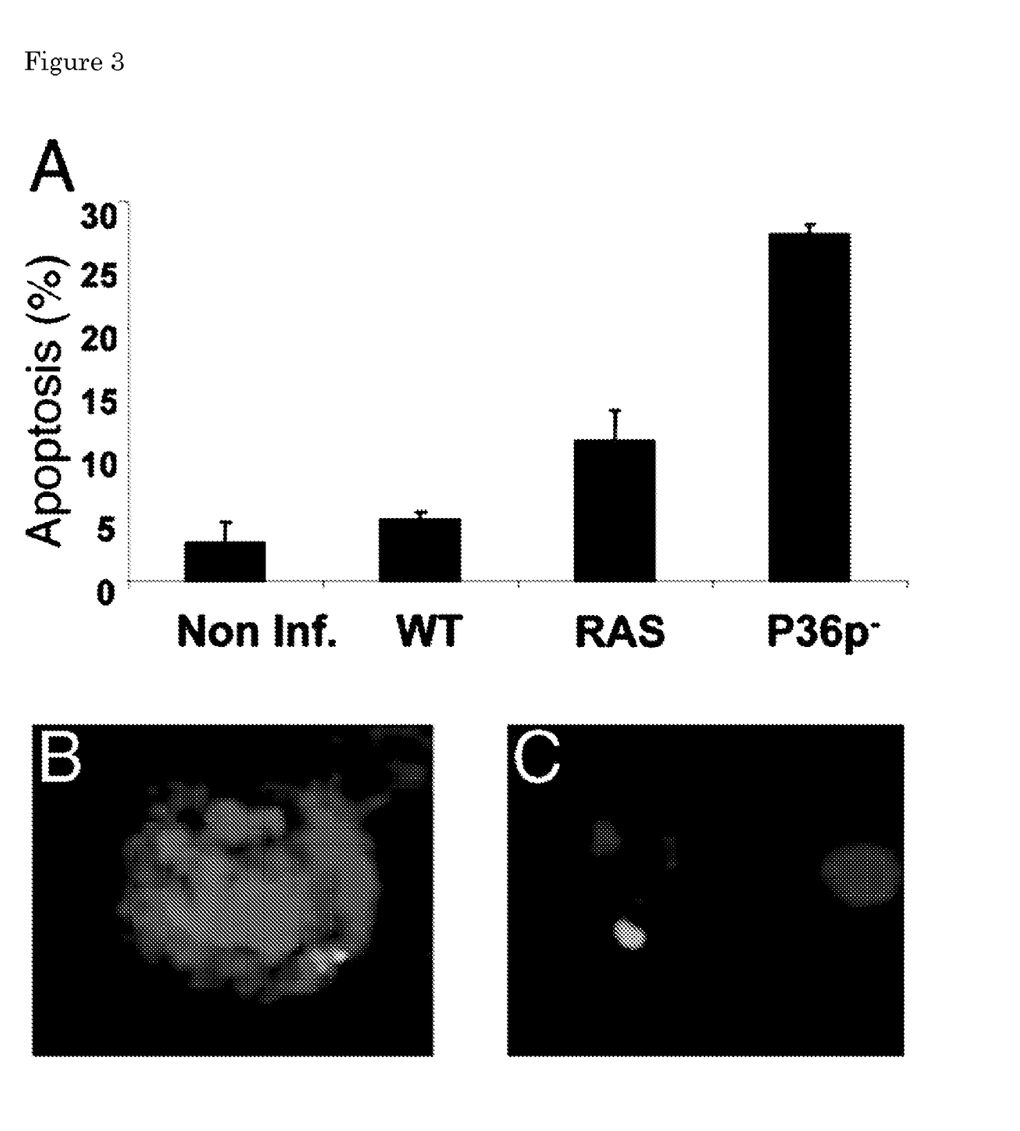
FIG. 3. Apoptosis is increased in p36p⁻ parasitized liver cells. (A) Apoptosis rates represent the percentage of parasite-invaded cells that undergo apoptosis 6 h after infection of HepG2 cells with WT, RAS, or p36p⁻ sporozoites. Non. Inf. indicates noninfected HepG2 cell cultures. Error bars represent SD. (B and C) Visualization of p36p⁻ sporozoite (green, anti-HSP70) infected hepatocytes displaying typical apoptotic signs as detected by DAPI staining (blue) in vitro (B) as well as in vivo (C). Active caspase-3 (red) detection was also performed in B. (Original magnification, ×1,260.)

Host hepatocyte apoptosis is normally inhibited by WT parasites upon invasion and establishment of the PV (34). Therefore, it was possible that the observed rapid disappearance of p36p⁻ sporozoite-infected HepG2 cells in culture was due to the inability of the parasite to prevent the hepatocyte from undergoing apoptosis. Consequently, the level of apoptosis in p36p⁻ sporozoite-invaded cells was examined (FIG. 3A). In three independent experiments, HepG2 cells were incubated with WT, RAS, or p36p⁻ sporozoites, and apoptosis was determined 6 h after infection by detection of active caspase-3 in the infected host cell cytoplasm and by analysis of the nuclear morphology of the infected cells after DAPI staining by observing chromatin condensation and/or nuclear fragmentation (FIG. 3B). Interestingly, we also detected apoptosis of p36p⁻ parasitized hepatocytes in vivo 6 h after infection (FIG. 3C). The level of apoptosis in p36p⁻ parasitized cells was significantly higher (P<0.05) compared to that in RAS-infected cells, which was higher than the level observed in WT-infected cells (FIG. 3A). The different levels of apoptosis are consistent with the observed longer survival time of RAS in culture (39).

Immunization with p36p⁻ Sporozoites Protects BALB/c and C57BL6 Mice Against Subsequent Infection.

Figure 4:
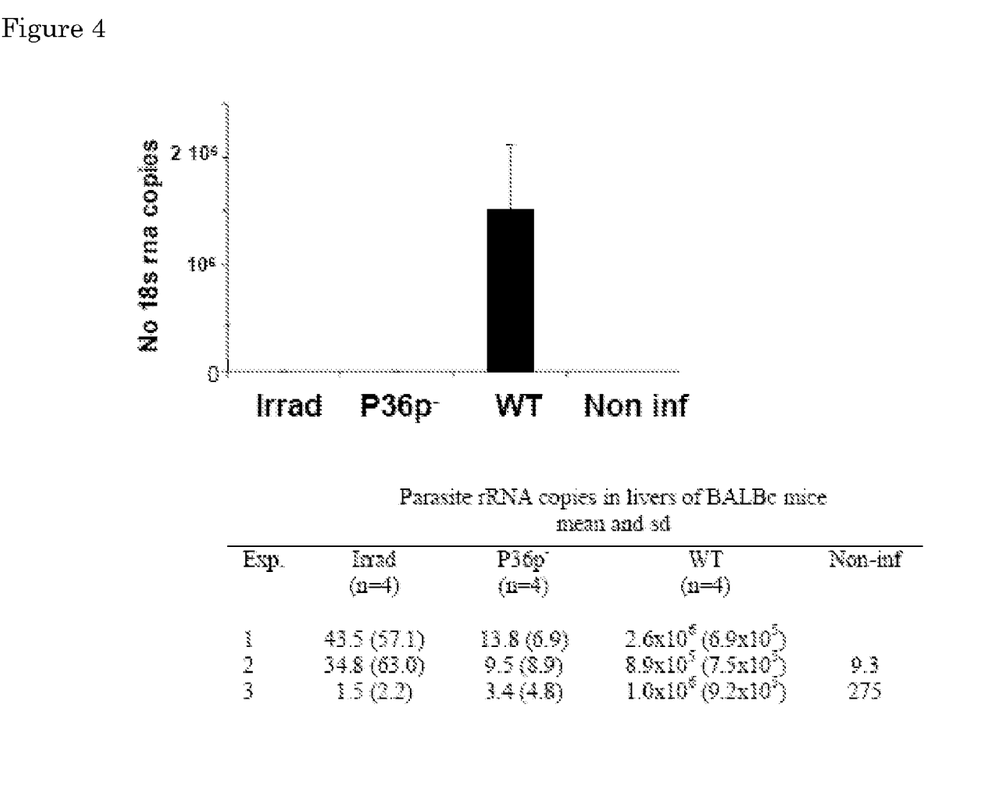
FIG. 4. Inhibition of liver stage development of wild type $Plasmodium$ $berghei$ in mice immunized with g-irradiated or with p36p⁻ sporozoites. Inhibition of development was determined by real-time PCR quantification of A-type 18S ribosomal RNA copies in liver stage parasites 40 h after the invasion of wild-type parasites. Groups of four BALB/c mice (for each condition) were immunized with $10^5$ p36p⁻ or $10^5$ g-irradiated sporozoites (Irrad) or with PBS and challenged with $5 \times 10^4$ wild-type (WT) sporozoites 10 days later. Error bars represent standard deviations.

Because RAS has been successfully used in immunization studies for generation of protection against subsequent challenge with WT sporozoites, we investigated the immunization potential of p36p⁻ sporozoites. Mice were i.v. immunized with p36p⁻ sporozoites by using different immunization protocols and subsequently challenged with WT parasites. Protection was determined by using two different detection assays. (i) In three independent experiments, groups of four BALB/c mice were infected with either $10^5$ p36p⁻ sporozoites or $10^5$ RAS. After 10 days, mice were challenged with $5\times10^4$ WT sporozoites and assessed for liver stage development by using real-time PCR assays to quantify A-type ribosomal RNA transcripts produced by developing trophozoites (36). Mice immunized with RAS and p36p⁻ sporozoites showed a very strong and comparable reduction (>99%) in liver stage development of WT parasites compared to nonimmunized mice (FIG. 4). (ii) In several independent experiments groups of BALB/c and C57BL6 mice were immunized with a single dose of 10 to $5\times10^4$ p36p⁻ sporozoites or multiple times (one to three immunizations) with 5 to $2\times10^4$ p36p⁻ sporozoites, respectively, and challenged with different doses of WT sporozoites on different days after immunization (Table 2). Protection was determined by monitoring mice intermittently for blood stage parasitemia in bloodsmears or using FACS analysis from day 3 to 3 weeks after challenge.

A single immunization dose of p36p⁻ sporozoites fully protected BALB/c mice (53 of 55) and induced a protective immune response that lasted for at least 4 months (120 days), whereas three subsequent immunizations with p36p⁻ sporozoites were required to completely protect C57BL6 mice (9 of 9), resulting in a protective immune response that lasted for at least one month (30 days), as shown by the absence of subsequent blood stage infection after challenge with WT sporozoites. Furthermore, in two nonprotected BALB/c mice (Table 2; experiment 1) liver development was strongly inhibited ($\approx 10^3$), as shown by a 3-day delay in patent parasitemia. Five protected BALB/c animals (Table 2; experiment 1) were rechallenged, 1 and 2 months after immunization, respectively, with WT sporozoites and did not develop blood stage infections up to 2 weeks after challenge. C57BL6 mice were partially protected when immunized only twice with either RAS (33%) or p36p⁻ sporozoites (25%) (Table 2).

The protective immune response induced by p36p⁻ sporozoites as well as RAS sporozoites seemed to be parasite stage-specific, because BALB/c mice were not protected from a challenge with parasite-infected red blood cells and developed a normal blood stage infection comparable to the control group (Table 2). The protective immune response lasts a long time (at least 6 months from the start of the immunization), which indicates that this mutant is a perfect candidate for prophylactic treatment.

Example 2

Construction of a p36⁻ Mutant

A DNA construct was made with vector pHTK (ref. 47) such that the gene will be irreversibly disrupted upon integration of the construct by double cross over homologous recombination. The 5' segment of Pfp36p was amplified from genomic DNA of 3D7 parasites with the primers 5'-GACCCCGCGGATGTATGTATTGGTGC-3' (SEQ ID NO:20) and 5'-GGACCGTTAACACCAAATCACAACCC-3' (SEQ ID NO:21). This ~600 bp fragment was introduced 5' of the hdhfr cassette between the SacII and HpaI sites of pHTK

TABLE 2

Immunization with p36p⁻ sporozoites protects against a subsequent infection with WT sporozoites

| Experiment no. | Mouse strain | Immunization,* RAS/p36p⁻ × $10^3$ | Challenge dose†, WT × $10^3$ | Time of challenge, days after final immunization | No. protected (no. challenged) | | |
|---|---|---|---|---|---|---|---|
| | | | | | Control | RAS | p36p⁻ |
| 1 | BALB/c | 100 | 50 | 10 | 0 (10) | ND | 18 (20) |
| 2 | BALB/c | 50 | 25 | 10 | 0 (15) | 15 (15) | 15 (15) |
| 3 | BALB/c | 50 | 10 | 10 | 0 (5) | ND | 5 (5) |
| 3 | BALB/c | 50 | 10 | 30 | 0 (5) | ND | 5 (5) |
| 3 | BALB/c | 50 | 10 | 60 | 0 (5) | ND | 5 (5) |
| 3 | BALB/c | 50 | 10 | 120 | 0 (5) | ND | 5 (5) |
| 4 | BALB/c | 50 | 1,000 iRBC | 10 | 0 (3) | 0 (5) | 0 (4) |
| 1 | C57BL6 | 50 | 10 | 10 | 0 (3) | 0 (3) | 0 (1) |
| 1 | C57BL6 | 50/20 | 10 | 10 | 0 (3) | 1 (3) | 1 (4) |
| 1 | C57BL6 | 50/20/20 | 10 | 10 | 0 (5) | 5 (5) | 4 (4) |
| 1 | C57BL6 | 50/20/20 | 10 | 30 | 0 (5) | 5 (5) | 5 (5) |

*Groups of mice were immunized intravenously with one of PBS (control), RAS, or p36p⁻ sporozoites isolated from different mosquito batches. Multiple immunizations with RAS or p36p⁻ sporozoites were administered at 7-day intervals.
†Mice were challenged with WT sporozoites or parasite infected red blood cell (iRBC) stages and the prepatent period monitored by either counting Giemsa-stained bloodsmears or FACS analysis. All control, unimmunized mice became positive on day 4 or 5 after challenge. Sporozoites were isolated from different mosquito batches.

generating the vector pHTKPfp36p5'. The 3' segment of the Pfp36p gene was amplified with the primers 5'-GGACCAC-CGGTCCTGACCCTTCATCAGATG-3' (SEQ ID NO:22) and 5'-GGACCGGGCGCCCGGGGCCAGAATGT-TCTTGTTCG-3' (SEQ ID NO:23). This ~600 bp fragment was introduced into the Xma I and AvrII sites of pHTKPfp36p5' generating the vector pHTKPfp36pko. Similar vectors have been made to disrupt both P36 and to disrupt both genes and generate a double knock-out parasite.

Example 3

Mutants of *P. falciparum*

*Plasmodium falciparum* asexual stages are maintained (Trager and Jensen, 1976) and sorbitol-synchronised (Lambros and Vanderberg, 1979) by standard procedures. 3D7 is a cloned line derived from NF54 and was obtained from Professor David Walliker at Edinburgh University. Predominantly ring-stage parasites are transfected with 100 μg of purified (Qiagen) plasmid DNA as described previously [BioRAD electroporator settings 0.31 kV, 960 μF used with 0.2-cm cuvettes]. Positive selection is with 10 nM WR99210, an antifolate drug which selects for the presence of the human dhfr gene. Transformants are obtained between 15 and 23 days following transfection. Drug resistant parasites are cloned by limiting dilution. Expanded clonal cultures at 1% parasitemia are then subjected to negative selection in the presence of the positive selection pressure (WR99210). Parasites are maintained on WR99210. The 3D7/pHTK-rh3 parasites are either not treated or treated with 4 μM ganciclovir for 6 days until parasites re-appear.

REFERENCES

1. Frevert, U. (2004) *Trends Parasitol.* 9, 417-424.
2. Mota, M. M., Hafalla, J. C. & Rodriguez, A. (2001) *Science* 291:141-144.
3. Sultan, A. A., Thathy, V., Frevert, U., Robson, K. J., Crisanti, A., Nussenzweig, V., Nussenzweig, R. S. & Menard, R. (1997) *Cell* 90:511-522.
4. Menard, R. (2001) *Cell Microbiol.* 3:63-73.
5. Matuschewski, K., Nunes, A. C., Nussenzweig, V. & Menard, R. (2002) *EMBO J.* 21:1597-1606.
6. Kappe, S. H., Buscaglia, C. A. & Nussenzweig, V. (2004) *Annu. Rev. Cell Dev. Biol.* 20:29-59.
7. Ishino, T., Yano, K., Chinzei, Y. & Yuda, M. (2004) *PLoS Biol.* 2:77-84.
8. Ishino, T., Chinzei, Y. & Yuda, M. (2004) *Cell Microbiol.* 6:1119-1125.
9. Khater, E. I., Sinden, R. E. & Dessens, J. T. (2004) *J. Cell Biol.* 167:425-432.
10. Yuda, M. & Ishino, T. (2004) *Cell Microbiol.* 6:1119-1125.
11. Tsuji, M., Rodrigues, E. G. & Nussenzweig, S. (2001) *Biol. Chem.* 382:553-570.
12. Luke, T. C. & Hoffman, S. L. (2003) *J. Exp. Biol.* 206:3803-3808.
13. Doolan, D. L. & Hoffman, S. L. (1999) *J. Immunol.* 163:884-892.
14. Tsuji, M. & Zavala, F. (2003) *Trends Parasitol.* 19:88-93.
15. Morrot, A. & Zavala, F. (2004) *Immunol. Rev.* 201:291-303.
16. Mueller, A.-K., Labaied, M., Kappe, S. H. I. & Matuschewski, M. (2005) *Nature* 433:164-167.
17. Mueller, A.-K., Camargo, N., Kaiser, K., Andorfer, C., Frevert, U., Matuschewski, K. & Kappe, S. H. (2005) *Proc. Natl. Acad. Sci. USA* 102:3022-3027.
18. Kappe, S. H., Gardner, M. J., Brown, S. M., Ross, J., Matuschewski, K., Ribeiro, J. M., Adams, J. H., Quackenbush, J., Cho, J., Carucci, D. J., et al. (2001) *Proc. Natl. Acad. Sci. USA* 98:9895-9900.
19. Le Roch, K. G., Zhou, Y., Blair, P. L., Grainger, M., Moch, J. K., Haynes, J. D., De La Vega., P, Holder, A. A., Batalov, S., Carucci, D. J. & Winzeler, E. A. (2003) *Science* 301:1503-1508.
20. van Dijk, M. R. Janse, C. J., Thompson, J., Waters, A. P., Braks, J. A., Dodemont, H. J., Stunnenberg, H. G., van Gemert, G.-J., Sauerwein, R. W. & Eling, W. (2001) *Cell* 104:153-164.
21. Thompson, J., Janse, C. J. & Waters, A. P. (2001) *Mol. Biochem. Parasitol.* 118:147-154.
22. Stowers, A. & Carter, R. (2001) *Exp. Opin. Biol. Ther.* 1:619-628.
23. Franke-Fayard, B., Trueman, H., Ramesar, J., Mendoza, J., van der Keur, M., van der Linden, R., Sinden, R. E., Waters, A. P. & Janse, C. J. (2004) *Mol. Biochem. Parasitol.* 137:23-33.
24. de Koning-Ward, T. F., Speranca, M. A., Waters, A. P. & Janse, C. J. (1999) *Mol. Biochem. Parasitol.* 100, 141-146.
25. de Koning-Ward, T. F., Fidock, D. A., Thathy, V., Menard, R., van Spaendonk, R. M., Waters, A. P. & Janse, C. J. (2000) *Mol. Biochem. Parasitol.* 106:199-212.
26. van Spaendonk, R. M., Ramesar, J., van Wigcheren, A., Eling, W., Beetsma, A. L., van Gemert, G.-J., Hooghof, J., Janse, C. J. & Waters, A. P. (2001) *J. Biol. Chem.* 276:22638-22647.
27. Menard, R. & Janse, C. J. (1997) *Methods* 13:148-157.
28. Janse, C. J. & Waters, A. P. (1997) *Parasitol. Today* 11:138-143.
29. Sinden, R. E. (1997) in *Molecular Biology of Insect Diseases Vectors: A Methods Manual*, eds. Crampton, J. M., Beard, C. B. & Louis, C (Chapman and Hall, London), pp. 67-91.
30. Ozaki, L. S., Gwadz, R. W. & Godson, G. N. (1984) *J. Parasitol.* 70:831-833.
31. Stewart, M. J. & Vanderberg, J. P. (1988) *J. Protozool.* 35:389-393.
32. Carrolo, M., Giordano, S., Cabrita-Santo, S. L., Corso, S., Vigario, A. M., Silva, S., Leiriao, P., Carapau, D., Armas-Portela, R., Comoglio, P. M., et al. (2003) *Nat. Med.* 9:1363-1369.
33. Silvie, O., Rubinstein, E., Franetich, J. F., Prenant, M., Belnoue, E., Renia, L., Hannoun, L., Eling, W., Levy, S., Boucheix, C. & Mazier, D. (2003) *Nat. Med.* 9:93-96.
34. Leiriao, P., Albuquerque, S. S., Corso, S., van Gemert, G.-J., Sauerwein, R. W., Rodriguez, A., Giordano, S. & Mota, M. (2005) *Cell Microbiol.* 7:603-609.
35. Orjih, A. U., Cochrane, A. H. & Nussenzweig, R. S. (1982) *Trans. R. Soc. Trop. Med. Hyg.* 76:57-61.
36. Bruna-Romero, O., Hafalla, J. C., Gonzalez-Aseguinolaza, G., Sano, G., Tsuji, M. & Zavala, F. (2001) *Int. J. Parasitol.* 31:1499-1502.
37. Suhrbier, A., Janse, C., Mons, B., Fleck, S. L., Nicholas, J., Davies, C. & Sinden, R. E. (1987) *Trans. R. Soc. Trop. Med. Hyg.* 81:907-909.[CrossRef]
38. Mota, M. M., Hafalla, J. C. & Rodriguez, A. (2002) *Nat. Med.* 8:1318-1322.
39. Scheller, L. F. & Azad, A. F. (1995) *Proc. Natl. Acad. Sci. USA* 92:4066-4068.

40. Chatterjee, S., Ngonseu, E., Van Overmeir, C., Correwyn, A., Druilhe, P. & Wery, M. (2001) *Afr. J. Med. Med. Sci.* 30:25-33.
41. Restifo, N. P. (2000) *Curr. Opin. Immunol.* 12:597-603.
42. Leitner, W. W., Hwang, L. N., Bergmann-Leitner, E. S., Finkelstein, S. E., Frank, S. & Restifo, N. P. (2004) *Vaccine* 22:1537-1544.
43. Leiriao, P., Mota, M. M. & Rodriguez, A. (2005) *J. Infect. Dis.* 191:1576-1581.
44. Luder, C. G. K., Gross, U. & Lopes, M. F. (2001) *Trends Parasitol.* 17:480-486.
45. Blaho, J. A. (2003) *Int. Rev. Immunol.* 22:321-326.
46. Levine, B. (2005) *Cell* 120:159-162.
47. Duraisingh M T, Triglia T, Cowman A F (2002) *Int. J. Parasitol* 32:81-89
48. Lambros and Vanderberg, (1979) *J. Parasitol.*, 65:418-420
49. Trager and Jensen, (1976) *Science* 193:673-675.
50. Fidock and Wellems, (1997) *Proc. Natl. Acad. Sci. USA* 94:10931-10936.

The invention claimed is:

1. A mutant of *Plasmodium* wherein expression of protein P36p has been disrupted.

2. The mutant of claim 1, wherein said disruption has been achieved by complete or partial deletion of the gene coding for said protein P36p.

3. The mutant of claim 1, in which further the expression of one or more proteins selected from the group consisting of P36, upregulated in infective sporozoites 3 (Uis3) and upregulated in infective sporozoites 4 (Uis4) has been disrupted.

4. The mutant of claim 3, wherein said disruption is achieved by complete or partial deletion of one or more of the genes coding for proteins selected from the group consisting of P36, Uis3 and Uis4.

5. The mutant of claim 1, wherein said mutant is a mutant of *Plasmodium falciparum* or *Plasmodium berghei*.

6. An immunological composition comprising the mutant of claim 1.

7. A vaccine for prevention of malaria caused by a species of *Plasmodium* comprising a sporozoite mutant of said species of *Plasmodium* wherein expression of protein P36p has been disrupted, a pharmaceutically acceptable carrier and an optional adjuvant.

8. The mutant of claim 1, which further comprises a heterologous antigen.

* * * * *